United States Patent
Cheney, III et al.

[11] Patent Number: 5,391,198
[45] Date of Patent: Feb. 21, 1995

[54] REUSABLE THERMAL COMPRESS

[76] Inventors: Henry H. Cheney, III, 19 Charles St., Braintree, Mass. 02184; Michael Vecchione, 106 Banwell La., Mt. Laurel, N.J. 08054

[21] Appl. No.: 197,244

[22] Filed: Feb. 16, 1994

[51] Int. Cl.⁶ .............................................. A61F 7/00
[52] U.S. Cl. ................................................. 607/114
[58] Field of Search ............... 607/96, 108–112, 607/114

[56] References Cited
U.S. PATENT DOCUMENTS 4,865,012 9/1989 Kelley ........................... 607/114 X
5,150,707 9/1992 Anderson ........................... 607/114

FOREIGN PATENT DOCUMENTS 56-20450 2/1981 Japan ..................... 607/114

Primary Examiner—Angela D. Sykes
Attorney, Agent, or Firm—John P. McGonagle

[57] ABSTRACT

A method of applying heat or cold to human or animal parts and a reusable compress utilized therein. The method involves saturating crystals of a water soluble acrylic polymer and a thickening agent through the porous fabric of a compress bag containing the acrylic polymer and the thickener. The compress is heated in a warm water or a microwave oven or cooled in a cool environment. The compress is applied to a human or animal part to warm or cool the body part. When the compress is no longer needed the gel is de-hydrated and the compress is easily stored for safe reuse.

5 Claims, 2 Drawing Sheets

REUSABLE THERMAL COMPRESS

BACKGROUND OF THE INVENTION

This invention relates to a thermal compress capable of being heated or cooled by various energy sources without the compress construction being adversely effected.

Compresses have been used to apply heat or cold therapy to human or animal body parts. The previous known compresses used polymer gels because of the high relative heat capacity of these materials. The gels are flexible allowing for better heat transfer ability to body parts. Unfortunately, the previous compresses are unwieldy to store because the gels are prehydrated. Some of the compresses use water as the internal fluid. While the heat capacity of water is relatively high, these water filled compresses can not be reused a great number of times due to potential leakage from the compresses.

Thermal compresses including a plastic envelope containing a gel capable of maintaining its gel-like consistency over a wide temperature range are known as evidenced by U.S. Pat. No. 3,885,403, granted May 27, 1975, and U.S. Pat. No. 4,756,311, granted Jul. 12, 1988. Hot and cold compresses including a rupturable container constructed of a laminated plastic sheet material and an outer layer of low density polyethylene are disclosed in U.S. Pat. No. 3,763,622, granted Oct. 9, 1973. Hot and cold compresses including containers or envelopes formed from laminated plastic sheets are also disclosed in U.S. Pat. No. 3,893,834.

In the gel based therapy device of U.S. Pat. No. 4,671,267, a pre-made mix of a humectant or moisturizing agent with a polymeric matrix is enclosed in a water impervious fabric. Heat or cold is applied to the U.S. Pat. No. 4,671,267 gel based therapy device and the therapy device is applied to the body part. The polymeric matrix maintains its gel qualities after use.

Other compresses have used gels for their heat capacity qualities. In the U.S. Pat. No. 4,756,311 microwaveable thermal compress, the gel is completely sealed in an envelope. The thermal compress can be microwaved and then applied to the body part for warming. Since the gel is sealed in the envelope, the gel is pre-saturated. As a result, storage of the compresses is cumbersome making repeated reuse of the compresses undesirable.

The instant invention thermal compress as disclosed herein is capable of various uses such as to warm body parts or to cool an injured part of the body. Most compresses currently being manufactured in the United States are made from sheets of plastic or from tubular extruded plastic. The plastic layers are sealed to form a closed envelope. The envelope is filled with a gel-like substance that can withstand temperatures without decomposing or losing its viscosity. Methods of heating the compresses include placing the compress in hot water, or placing the compress into a microwave oven. The compress is cooled by placing the compress in the freezer compartment of a refrigerator. During these methods the gel is put under stress and can lose its viscosity. This causes the compress to have erratic performance. The compress plastic also loses its strength with repeated use.

SUMMARY OF INVENTION

The present invention is directed to a method of applying heat or cold to human or animal parts and to the reusable thermal (hot or cold) compresses utilized therein. The method involves saturating crystals of a water soluble acrylic polymer and a thickening agent through the porous fabric of a compress bag containing the acrylic polymer and the thickener. The compress may be heated in a microwave oven or cooled in a cool environment. The compress is applied to a human or animal part to warm or cool the body part. When the compress is no longer needed the gel is de-hydrated and the compress is easily stored for safe reuse.

More particularly, this invention involves a water porous fabric compress which contains relatively large dehydrated crystals of a water soluble acrylic polymer and a thickening agent. Due to the fact the crystals are not pre-hydrated the compress may be easily stored for use. When compress use is needed, the compress is placed in a container of water to completely saturate the polymer to form a gel. In this way, there is little danger of bacteria or impurities becoming trapped in the polymer once it is applied to an environment such as a refrigerator. The compress is then applied to a body part to warm or cool the body part. After use, the compress will de-saturate with the water diffusing out of the bag. The crystals of water soluble acrylic polymer will remain in the bag due to their size and the porosity of the compress bag fabric. The compress of the instant invention is also safer than the prior art plastic compresses. Prior art compresses often rupture when heated in a microwave for over a minute due to the expansion of trapped and heated air against the impervious plastic bag. The compress of the instant invention will not rupture from heating, because expanding hot air seeps through the fabric.

The present invention makes three major improvements to prior art compresses. First, the compress is made out of fabric and not plastic thereby providing a more pleasant tactile sensation for the patient. Second, the gel is formulated using a water soluble acrylic polymer which is unaffected by extreme temperatures. Third, the freight cost to get the product to the patient is greatly reduced. Another advantage is that the acrylic polymer will absorb topical medications and fragrances.

The present invention's use of fabric in place of plastic brings a new level of comfort to the patient. Most of the prior art plastic compresses suggest placing the compress into a towel before applying it to a patient's skin. Since the present invention is made from fabric, it is not necessary to wrap the compress in a towel. The present invention fabric is woven so that when used as a hot compress it will provide the patient with moist heat which is an additional benefit not available from compresses made from plastic. Previously the only way to obtain moist heat was from wet towels soaked in hot water or hydroculator compresses which require the purchase of a hydroculator which costs thousands of dollars. The fabric compress of the instant invention is also more durable therefore increasing the useful life of the product.

When the instant invention is reused as a cold compress it is first placed into a cooling chamber such as a freezer to become cold. The gel-like substance becomes cold like any of the traditional reusable cold compresses. The advantage of the present invention is that when cold it can be applied directly to the skin and does not have a clammy or slippery feeling from the condensation coming from the exterior of a prior art plastic envelope. This is a substantial improvement over current compresses. The third advantage of less freight costs comes about because the present invention compress can be shipped without the gel being formed. Two pieces of fabric are stitched on three sides. The chemical in its dry form is inserted into the compress and the open end is closed by stitching. The resulting product weighs less than 4 ounces. Current compresses weigh a pound. To activate the instant invention fabric compress, the patient soaks the compress in water until it reaches the desired size. A major advantage of this method of activation is that the cost of shipping the fabric product to the medical distributor is reduced by 400 percent.

Various advantages and features of novelty which characterize the invention are pointed out with particularity in the claims annexed hereto and forming a part thereof. However for a better understanding of the invention, its advantages and objects obtained by its use, reference should be made to the drawings, which form a further part here of, and to the accompanying descriptive matter, in which there is illustrated and described a preferred embodiment of the invention.

DETAILED DESCRIPTION OF THE INVENTION

Figure 1:
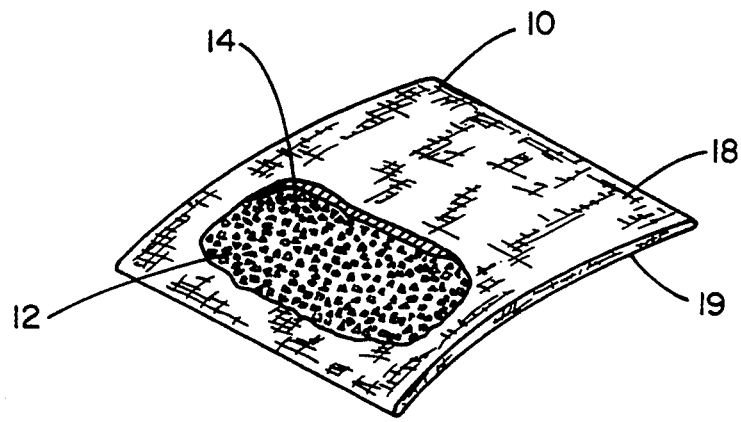
FIG. 1 is a perspective view of a compress according to the principles of the present invention, with a portion cut-away merely for illustrative purposes, said compress being shown in its pre-hydration stage.
Figure 3:
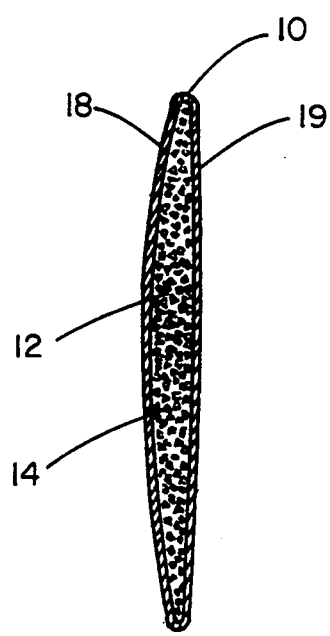
FIG. 3 is a cross-sectional view of the compress of FIG. 1.

Referring to the drawings in detail wherein like elements are indicated by like numerals, the instant invention reusable thermal compress is comprised of a water porous fabric bag 10 containing relatively large crystals 12 of a water soluble acrylic polymer and a thickening agent 14. See FIGS. 1 and 3. The bag 10 is porous enough to allow water (not shown) to enter or exit, but not to let the crystals 12 and thickener 14 pass through. The fabric bag 10 may be a spunlaced fabric such as that sold under the trademark SONTARA by DuPont, or any other similar fabric. The crystals 12 are of a small enough size to rapidly hydrate when exposed to water but large enough to remain contained in the porous fabric bag 10 when the crystals 12 are not hydrated.

Figure 2:
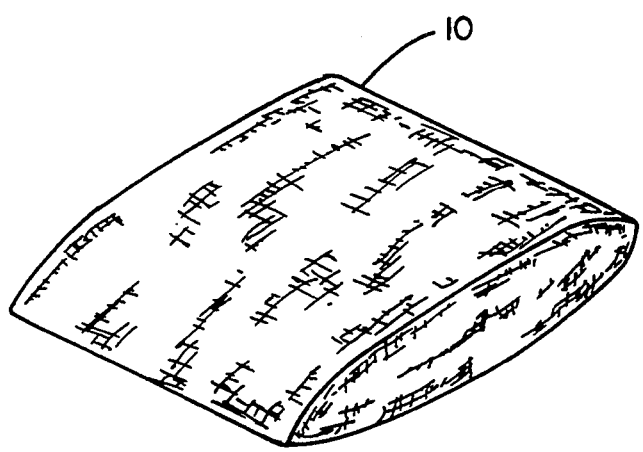
FIG. 2 is a view of the compress of FIG. 2 after hydration.
Figure 4:
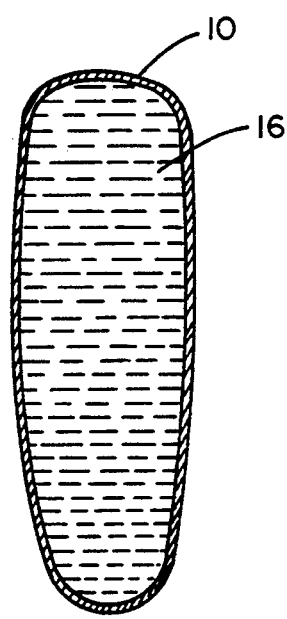
FIG. 4 is a cross-sectional view of the compress of FIG. 2.

One of the known qualities of water soluble acrylic polymers is the ability of the polymers to absorb water. When the porous fabric bag 10 containing the water soluble acrylic polymer 12 is placed in a container of water, the water will enter through the porous fabric and rapidly hydrate the water soluble acrylic polymer and thickener, resulting in a gel 16. See FIGS. 2 and 4. The gelled acrylic polymer will hold moisture and has good heat capacity characteristics. A thickening agent is added to further enhance the water absorption qualities of the crosslinked modified acrylic polymer.

The compress bag 10 is fabricated from two pieces of fabric 18, 19. The fabric is lock stitched on three sides to form an envelope. The envelope is filled with three ounces of crosslinked modified acrylic polymer. The open side is lock-stitched closed thereby forming a bag.

The compress is activated by soaking the compress in any temperature of water. The compress will absorb the water forming a compress equal in size to the ones currently on the market. The chemicals contained within the compress are non-toxic so there is no potential harm to the using patient. Should the compress chemicals come out of the compress they are easy to clean up versus the current ones on the market which create a mess and are very difficult to clean up.

In a preferred embodiment of the reusable hot or cold compress, the porous fabric bag contains 0.2 to 5 ounces of a crosslinked modified acrylic polymer in a granular size of 2 to 4 millimeters across, commercially sold as SOILMOIST, and 1 to 2 cubic centimeters of trisaminothane as the thickening agent.

In use the reusable thermal compress is placed in a container of water. The water enters through the porous fabric of the bag, hydrating the water soluble acrylic polymer. The hydrated acrylic polymer with the thickening agent forms a water saturated gel, which expands to fill the fabric bag in approximately 20 minutes. The porous bag containing the gelled acrylic polymer and the thickening agent can then be heated, e.g., in a conventional microwave oven, for warming. The reusable thermal compress is then applied to a human or animal body part. Due to the flexibility of the compress gel, the reusable thermal compress fits snugly against the body part for enhanced heat transfer characteristics. Since the acrylic polymer is completely saturated, bacteria or other impurities are less likely to be absorbed by the polymeric matrix. When the heat dissipates or body part warming is no longer necessary, the compress is removed from the body part. If further warming is necessary, then the reusable thermal compress may be reheated and reapplied to the body part. If the reusable thermal compress is no longer necessary, the compress is placed in a sink or drainage. The water soluble acrylic polymer will eventually release the water through the fabric bag. The reusable compress consisting of the porous fabric bag containing the de-hydrated acrylic polymer and the trisaminothane may then be easily stored without any concerns about liquid leakage.

The instant invention reusable thermal compress may also be used for cooling a human or animal body part. After the gel is formed in the porous bag, the compress is placed in a cold environment such as a refrigerator or freezer. The cooled compress is then applied to a body part thereby cooling the body part. Once the compress is no longer needed for cooling, dehydration and storage is accomplished in a similar method as when the compress is used for warming.

The instant invention has been tested for performance against plastic ones currently on the market. The following results were obtained:

TABLE 1

| | COLD COMPRESS** | |
|---|---|---|
| Minutes out of Freezer | Temperature of Fabric Compress | Temperature of Plastic Compress |
| 5 | 7.4° | 4.0° |
| 10 | 8.2° | 6.0° |
| 15 | 11.4° | 8.2° |
| 20 | 19.0° | 9.4° |
| 25 | 21.4° | 10.8° |

**Freezer Temperature = 7.0° Fahrenheit
Ambient Temperature = 72.0° Fahrenheit
All temperatures indicated as Fahrenheit.

TABLE 2

| | HOT COMPRESS** | |
|---|---|---|
| Minutes out of Microwave | Temperature of Fabric Compress | Temperature of Plastic Compress |
| 5 | 111.2° | 106.6° |
| 10 | 110.8° | 108.2° |
| 15 | 110.2° | 106.8° |
| 20 | 110.0° | 105.0° |
| 25 | 109.2° | 103.8° |

**Compress placed in 900 Watt Microwave Oven for 2 minutes.
All temperatures indicated as Fahrenheit.

It is understood that the above embodiment using SOILMOIST as the water soluble acrylic polymer and trisaminothane as the thickening agent are merely illustrative of the invention. Other embodiments may be readily devised by those skilled in the art which will embody the principles of the invention and fall within the spirit and scope thereof.

We claim:

1. A reusable thermal compress used in the process of cooling or warming a human or animal body part comprising:
   a water porous fabric bag;
   a plurality of dehydrated water soluble acrylic polymer crystals contained within said bag and of large enough size to remain contained within said bag, wherein said water soluble acrylic polymer is a crosslinked modified acrylic polymer; and
   a thickening agent contained within said fabric bag, wherein said thickening agent is trisaminothane.

2. A reusable thermal compress as recited in claim 1, wherein:
   said water soluble acrylic polymer crystals have a granular size of from two to four millimeters in diameter.

3. A reusable thermal compress as recited in claim 2, wherein:
   said fabric bag contains 0.2 to 5 ounces of a crosslinked modified acrylic polymer in a granular size of 2 to 4 millimeters in diameter, and 1 to 2 cubic centimeters of trisaminothane.

4. A process for warming human or animal body parts, comprising the steps of:
   placing a reusable thermal compress comprised of a water porous fabric bag containing crosslinked modified acrylic polymer crystals large enough to be contained within said bag and a trisaminothane thickening agent into water;
   saturating said compress with water until a saturated gel is formed within said bag;
   warming said compress with an external source;
   applying said compress to a body part to be warmed;
   drying said compress until said crosslinked modified acrylic polymer is dehydrated; and
   storing said compress for reuse.

5. A process for cooling human or animal body parts, comprising the steps of:
   placing a reusable thermal compress comprised of a water porous fabric bag containing crosslinked modified acrylic polymer crystals large enough to be contained within said bag and a trisaminothane thickening agent into water;
   saturating said compress with water until a saturated gel is formed within said bag;
   cooling said compress with an external source;
   applying said compress to a body part to be warmed;
   drying said compress until said crosslinked modified acrylic polymer is dehydrated; and
   storing said compress for reuse.

* * * * *